(12) United States Patent
Matsuo et al.

(10) Patent No.: US 7,147,668 B2
(45) Date of Patent: *Dec. 12, 2006

(54) HAIR BLEACH

(75) Inventors: Takashi Matsuo, Tokyo (JP); Hajime Miyabe, Tokyo (JP); Yutaka Shibata, Tokyo (JP)

(73) Assignee: KAO Corporation, Tokyo (JP)

( * ) Notice: Subject to any disclaimer, the term of this patent is extended or adjusted under 35 U.S.C. 154(b) by 133 days.

This patent is subject to a terminal disclaimer.

(21) Appl. No.: 10/275,736

(22) PCT Filed: Jun. 8, 2001

(86) PCT No.: PCT/JP01/04835

§ 371 (c)(1),
(2), (4) Date: Nov. 8, 2002

(87) PCT Pub. No.: WO01/95869

PCT Pub. Date: Dec. 20, 2001

(65) Prior Publication Data

US 2003/0192133 A1     Oct. 16, 2003

(30) Foreign Application Priority Data

Jun. 12, 2000  (JP) .............................. 2000-175133
Jun. 12, 2000  (JP) .............................. 2000-175134

(51) Int. Cl.
*D06L 3/00* (2006.01)

(52) U.S. Cl. ..................... 8/101; 8/107; 8/111; 424/62

(58) Field of Classification Search .................... 8/405, 8/406, 435, 540, 547, 554, 606, 101, 107, 8/111; 424/62
See application file for complete search history.

(56) References Cited

U.S. PATENT DOCUMENTS 3,981,678 A      9/1976  Ghilardi et al. ................. 8/11
4,314,808 A *    2/1982  Jacquet et al. ................. 8/405
4,470,826 A *    9/1984  Bugaut et al. .................. 8/115
4,736,067 A      4/1988  Bugaut et al. ............... 564/369
6,071,504 A      6/2000  Kawai et al. ............. 424/70.12
6,540,791 B1 *   4/2003  Dias ............................... 8/111
6,916,432 B1 *   7/2005  Matsuo et al. ........... 252/186.1

FOREIGN PATENT DOCUMENTS

| DE | 100 08 640 | 8/2000 |
| EP | 806198 | 11/1997 |
| JP | 59-106413 | 6/1984 |
| JP | 1-213220 | 8/1989 |
| JP | 5-246827 | 9/1993 |
| WO | WO 96/29976 | 10/1996 |

* cited by examiner

Primary Examiner—Eisa Elhilo
(74) Attorney, Agent, or Firm—Oblon, Spivak, McClelland, Maier & Neustadt, P.C.

(57) ABSTRACT

An oxidative hair bleach comprising a first pack with an alkalizing agent contained therein and a second pack with an oxidizing agent contained therein, wherein the oxidative hair bleach comprises the following ingredients (A), (B), (C), (D) and (E) in the following proportions in a whole composition after mixing the first pack and the second pack together, and has a pH of from 8 to 12:

(A) a water-miscible organic solvent having an octanol-water distribution coefficient (log P) at 25° C. of 0.3 or greater and a molecular weight of 200 or lower: 8 to 40 wt. %;

(B) the alkalizing agent: 0.1 to 10 wt. %;

(C) the oxidizing agent: 0.1 to 12 wt. % as calculated in terms of hydrogen peroxide;

(D) water: 25 to 70 wt. % and (E) an anionic surfactant or ampholytic surfactant in a proportion of 60 wt. % or less in said whole composition after mixing said first pack and said second pack together.

This hair bleach has excellent bleaching power and can color hair into a light tone and a good shade, and has a reduced irritating odor and is low in irritation to the scalp.

18 Claims, No Drawings

HAIR BLEACH

TECHNICAL FIELD

This invention relates to a hair bleach excellent in bleaching power for hair or the like or a hair dye excellent in dyeing power for hair or the like, which has a predetermined octanol-water partition coefficient or greater and contains a low-molecular, water-miscible organic solvent.

BACKGROUND ART

As oxidative hair bleaches or hair dyes, those of the two-pack type, each comprising a first pack with an alkalizing agent contained therein and a second pack with an oxidizing agent contained therein, are widely used. The alkalizing agent in the first pack is incorporated to obtain a light tone by heightening beaching or dyeing effect and causing oxidative decomposition of melamine granules to proceed in hair. To bleach or dye hair into a tone lighter than his or her own hair color, sufficient bleaching power is needed. When an oxidative hair bleach or hair dye is used for such purposes, alkali is required in a particularly sufficient amount because hair bleaching power generally depends upon the amount of alkali.

Conventionally, ammonia has been used as an alkali agent in general. However, ammonia has a strong irritating odor and hence, involves a drawback that it gives considerable unpleasant feeling upon bleaching or dyeing.

Attempts have, therefore, been made to use organic amines of a lower irritating odor in place of ammonia (JP-A-59106413, JP-A-01213220, JP-A-05246827, etc.). These attempts, however, cannot bleach hair into a sufficiently light shade and moreover, use of such organic amines in large amounts, due to their high remaining tendency on the scalp, leads to a problem that irritation tends to be given.

DISCLOSURE OF THE INVENTION

An object of the present invention is, therefore, to provide a hair bleach or hair dye, which has excellent bleaching power, can dye hair in a light tone and good shade, and has a reduced irritating odor and is low in irritation to the scalp.

The present inventors have found that inclusion of a specific water-miscible organic solvent in a particular proportion in an oxidative hair bleach or an oxidative hair dye makes it possible to provide the treatment with increased hydrophobicity and hence to promote transferability of the bleach (an alkalizing agent and an oxidizing agent) into hair and as a result, makes it possible to achieve the above-described object.

The present invention provides an oxidative hair bleach or hair dye comprising a first pack with an alkalizing agent contained therein and a second pack with an oxidizing agent contained therein, wherein the oxidative hair bleach or hair dye comprises the following ingredients (A), (B), (C) and (D) in the following proportions in a whole composition after mixing the first pack and the second pack together, and has a pH of from 8 to 12:

(A) a water-miscible organic solvent having an octanol-water distribution coefficient (log P) at 25° C. of 0.3 or greater and a molecular weight of 200 or lower: 8 to 40 wt. %

(B) the alkalizing agent: 0.1 to 10 wt. %

(C) the oxidizing agent: 0.1 to 12 wt. % as calculated in terms of hydrogen peroxide (D) water: 25 to 70 wt. %.

The present invention also provides a method for bleaching or dyeing hair, which comprises applying the above-described bleach or dye to the hair.

BEST MODES FOR CARRYING OUT THE INVENTION

Concerning the water-miscible organic solvent as the ingredient (A), the term "log P" is an indicator of partition of a substance between an octanol phase and a water phase, and is defined by the below-described formula. Examples of its calculated values and measured values are disclosed in A. Leo, C. Hash, and D. Elkins: "Chemical Reviews", 71(6), (1971). In the present invention, however, it means a value as measured at 25° C. in accordance with the method described in The Law Concerning the Examination and Regulation of Manufacture of Chemical Substances, Revised 4$^{th}$ Edition, "Measuring Method of Partition Coefficients of Chemical Substances (in 1-Octanol/Water) <Part 1>" (Published by The Chemical Daily Co., Ltd.)

$$\log P = \log([\text{substance}]_{octanol}/[\text{substance}]_{water})$$

wherein [substance]$_{octanol}$ means the molar concentration of the substance in the octanol phase and [substance]$_{water}$ means the molar concentration of the substance in the water phase.

log P (25° C.) of the water-miscible organic solvent for use in the present invention is required to be 0.3 or greater, preferably from 0.8 to 1.3 from the viewpoint of good transferability of the bleach to hair. From the viewpoint of bleaching power, on the other hand, the molecular weight of the organic solvent is required to be 200 or lower, preferably 185 or lower, more preferably 160 or lower. Examples of such water-miscible organic solvents can include benzyl alcohol (log P at 25° C.=1.1; this applies equally hereinafter), 2-benzyloxy ethanol (1.2), ethylene glycol mono-n-butyl ether (0.8), diethylene glycol mono-n-butyl ether (0.9), and n-butanol (0.8). Among these, benzyl alcohol and 2-benzyoxy ethanol are preferred. These organic solvents can be used either singly or in combination, and from the standpoint of providing sufficient bleaching or dyeing effect, the content of the water-miscible organic solvent can be from 8 to 40 wt. % based on the whole composition formed in combination of the first pack and the second pack, with 10 to 40 wt. %, especially 10 to 25 wt. % being preferred.

Illustrative of the alkalizing agent as the ingredient (B) are alkalizing agents other than ammonia, specifically alkanolamines such as monoethanolamine and isopropanolamine, and guanidinium salts such as guanidine carbonate. Of these, alkanolamines are preferred, with monoethanolamine being particularly preferred. These alkalizing agents can be used either singly or in combination. From the standpoint of providing sufficient bleaching or dyeing effect and also reducing irritation to the scalp, the content of the alkalizing agent may be from 0.1 to 10 wt. % based on the whole composition formed in combination of the first pack and the second pack, with 0.5 to 5 wt. %, especially 1 to 3 wt. % being preferred. The hair bleach or hair dye according to the present invention can bring about sufficient bleaching or dyeing effect without using ammonia as an alkalizing agent, and is completely free of an ammonia-derived irritating odor and gives no unpleasant feeling during use. Accordingly, the hair bleach or hair dye according to the present invention is preferable. Incidentally, still stronger bleaching or dyeing effect is available from use of ammonia. When ammonia is used, its proportion, from the standpoint of reducing its irritating odor, may preferably be from 0.01 to 3 wt. %, notably from 0.1 to 1 wt. % based on the whole composition formed in combination of the first pack and the second pack.

The alkalizing agent can be used preferably in such an amount that the free alkali value in the first pack in which the alkalizing agent is incorporated falls within a range of from 1 to 10, especially from 2 to 8. A free alkali value smaller than 1 cannot bring about sufficient bleaching or dyeing effect, while a free alkali value greater than 10 leads to stronger irritation to the scalp.

The term "free alkali value" as used herein means a value measured as will be described next. Described specifically, about 1 g of a sample (first pack) was taken. It was accurately weighed, followed by dissolution in deionized water (50 mL). Using 0.1 N hydrochloric acid, titration was conducted with an end point being set at pH 7, and a free alkali value was calculated in accordance with the following formula:

$$\text{Free alkali value} = (Y \times 0.1)/X$$

wherein X represents the amount (g) of the sample, and Y represents the consumption (mL) of 0.1 N hydrochloric acid.

Examples of the oxidizing agent as the ingredient (C) can include oxygen peroxide, urea peroxide, melamine peroxide, sodium perborate, potassium perborate, sodium percarbonate, and potassium percarbonate, with hydrogen peroxide being particularly preferred. From the standpoint of providing sufficient bleaching or dyeing effect and also reducing irritation to the scalp, the content of the oxidizing agent may be from 0.1 to 12 wt. % based on the whole composition formed in combination of the first pack and the second pack, with 2 to 12 wt. % being preferred.

The content of water as the ingredient (D), from the standpoint of providing sufficient bleaching or dyeing effect, may range from 25 to 70 wt. % based on the whole composition formed in combination of the first pack and the second pack, with 20 to 60 wt. %, especially 30 to 55 wt. % being preferred.

Further incorporation of an anionic surfactant or an ampholytic surfactant as an ingredient (E) in the hair bleach or hair dye according to the present invention makes it possible to improve the bleaching or dyeing effect and also to improve the storage stability. An anionic surfactant is particularly preferred for its low irritation to the scalp. Illustrative of the anionic surfactant are alkyl sulfate ester salts such as sodium lauryl sulfate, alkyl ether sulfate ester salts such as sodium polyoxyethylene lauryl sulfate, N-acylated glutamate salts such as monosodium N-lauroyl glutamate, N-acylated sarcocinates, alkyl ether phosphate salts, alkyl ether sulfosuccinate salts, and alkylbenzene sulfonate salts. Among these, alkyl ether sulfate ester salts and N-acylated glutamate salts being preferred. Illustrative of the ampholytic surfactant are alkylamide propylbetaine such as lauramide propylbetaine, alkylimidazolinium betaines such as 2-alkyl-N-carboxymethyl-N-hydroxyethylimidazolinium betaine, alkyldimethylaminoacetic acid betaines, and alkylhydroxy-sulfobetaines. Among these, alkylamidopropylbetaines and alkylimidazolinium betaines are preferred. As the ingredient (E), it is also possible to use an anionic surfactant and an ampholytic surfactant in combination or to use two or more compounds in combination. From the standpoint of providing sufficient bleaching or dyeing effect and also storage stability, the content of the ingredient (E) may be from 0 to 60 wt. % based on the whole composition formed in combination of the first pack and the second pack, with 5 to 60 wt. %, especially 10 to 30 wt. % being preferred.

Further incorporation of a quaternized-nitrogen-atom-containing polymer as an ingredient (F) can provide the hair bleach or hair dye according to the present invention with improved bleaching or dyeing effect and post-dyeing hair conditioning effect. Its effects can be heightened further when used in combination with an anionic surfactant. Examples of the quaternized-nitrogen-atom-containing polymer can include cationized cellulose derivatives [as commercial products, "LEOGUARD G" and "LEOGUARD GP" (products of Lion Corporation), "Catinal LC-100", "Polymer JR-125", "Polymer JR-400", "Polymer JR-30M", "Polymer JR-400" and "Polymer LR-30M" (products of Union Carbide Corp.), and "Celquat H-100" and "Celquat L200" (products of National Starch and Chemical Company); cationized polysaccharides [as commercial products, "Jaguar C-13S", "Jaguar C-14S", "Jaguar C-17", "Jaguar C-162", "Jaguar C-210" and "Jaguar HI-CARE 1000" (products of Rhone-Poulenc S.A.)]; diallyl dialkyl quaternary ammonium salt derivatives [as commercial products, "Merquat 100", "Merquat 280", "Merquat 295" and "Merquat 550" (products of BF Goodrich Co.)]; cationized polyvinyl-pyrrolidone derivatives [as commercial products, "Gafquat 734", "Gafquat 755" and "Gafquat 755N" (products of ISP Japan Ltd.)]. Among these, diallyl dialkyl quaternary ammonium salt derivatives are preferred. These cationic polymers can be used either singly or in combination. From the standpoint of providing sufficient bleaching or dyeing effect and post-dyeing hair conditioning effect, the content of the quaternary-nitrogen-atom-containing polymer may be preferably from 0 to 2.5 wt. %, more preferably from 0.3 to 2 wt. %, notably from 0.3 to 1 wt. % based on the whole composition formed in combination of the first pack and the second pack.

When the invention product is a hair dye, an oxidative dye intermediate or a direct dye is incorporated. When the invention product is a hair bleach, on the other hand, neither of these are incorporated.

As such an oxidative dye intermediate, known color developing substance and coupling substance, which are commonly employed in oxidative hair dyes, can be used. Illustrative of the color developing substance are p-phenylenediamines each of which contains one or more of $NH_2$— groups, NHR— groups and $NR_2$ groups (R represents an alkyl or hydroxyalkyl group having 1 to 4 carbon atoms), such as p-phenylenediamine, p-toluylenediamine, N-methyl-p-phenylenediamine, N,N-dimethyl-p-phenylenediamine, N,N-diethyl-2-methyl-p-phenylenediamine, N-ethyl-N-(hydroxyethyl)-p-phenylene-diamine, chloro-p-phenylenediamine, 2-(2'-hydroxyethyl-amino)-5-aminotoluene, N,N-bis-(2-hydroxyethyl)-p-phenylenediamine, methoxy-p-phenylenediamine, 2,6-dichloro-p-phenylenediamine, 2-chloro-6-bromo-p-phenylenediamine, 2-chloro-6-methyl-p-phenylenediamine, 6-methoxy-3-methyl-p-phenylenediamine, 2,5-diaminoanisole, N-(2-hydroxypropyl)-p-phenylenediamine, and N-2-methoxyethyl-p-phenylenediamine; 2,5-diaminopyridine derivatives; p-aminophenols and o-aminophenols, such as p-aminophenol, 2-methyl-4-aminophenol, 3-methyl-4-aminophenol, 2-chloro-4-aminophenol, 3-chloro-4-aminophenol, 2,6-dimethyl-4-aminophenol, 3,5-dimethyl-4-aminophenol, 2,3-dimethyl-4-aminophenol, 2,5-dimethyl-4-aminophenol, 2,4-diaminophenol, and 5-aminosalicylic acid; and o-phenylenediamines.

Illustrative of the coupling substance, on the other hand, are α-naphthol, o-cresol, m-cresol, 2,6-dimethylphenol, 2,5-dimethylphenol, 3,4-dimethylphenol, 3,5-dimethyiphenol, benzcatechin, pyrogallol, 1,5-dihydroxynaphthalene, 1,7-dihydroxynaphthalene, 5-amino-2-methylphenol, 5-(2'-hydroxyethylamino)-4-methoxy-2-methylphenol, hydroquinone, 2,4-diaminoanisole, m-toluylenediamine, 4-aminophenol, resorcin, resorcin monomethyl ether, m-phenylenediamine, 1-phenyl-3-methyl-5-pyrazolone, 1-phenyl-3-amino-5-pyrazolone, 1-phenyl-3,5-diketopyrazolone, 1-methyl-7-dimethylamino-4-hydroxy-2-quinolone, m-aminophenol, 4-chlororesorcin, 2-methylresorcin, 2,4-diaminophenoxyethanol, 2,6-diaminopyridine, 3,5-diaminotrifluoromethylbenzene, 2,4-diaminofluorobenzene, 3,5-diaminofluorobenzene, 2,4-diamino-6-hydroxypyrimidine, 2,4,6-triaminopyrimidine, 2-amino-4,6-dihydroxypyrimidine, 4-amino-2,6-dihydroxy-pyrimidine, and 4,6-diamino-2-hydroxypyrimidine.

Color developing substances and coupling substances can be used either singly or in combination, respectively. Their contents may each be from 0.01 to 5 wt. % based on the whole composition formed in combination of the first pack and the second pack, with 0.1 to 4 wt. % being particularly preferred.

As the direct dye, on the other hand, known acidic dyes, basic dyes, disperse dyes, reactive dyes and the like, which are usable in hair dyes, cam be used. Illustrative of the acidic dyes are Acid Red 27 (C.I. 16185), Acid Red 51 (C.I. 45430), Acid Red 18 (C.I. 16255), Acid Red 92 (C.I. 45410), Acid Red 94 (C.I. 45440), Acid Red 52 (C.I. 45100), Acid Yellow 23 (C.I. 19140), Food Yellow 3 (C.I. 15985), Food Green 3 (C.I. 42053), Food Blue 2 (C.I. 42090), Acid Blue 74 (C.I. 73015), Pigment Red 57-1 (C.I. 15850), Acid Red 33 (C.I. 17200), Acid Red 87 (C.I. 45380), Acid Red 92 (C.I. 45410), Acid Red 94 (C.I. 45440), Acid Orange 7 (C.I. 15510), Acid Red 95 (C.I. 45425), Acid Yellow 73 (C.I. 45350), Acid Yellow 3 (C.I. 47005), Acid Green 25 (C.I. 61570), Solvent Green 7 (C.I. 59040), Acid Green 5 (C.I. 42095), Acid Blue 5 (C.I. 42052), Acid Blue 9 (C.I. 42090), Acid Orange 24 (C.I. 20170), Acid Violet 9 (C.I. 45190), Food Red 6 (C.I. 16155), Acid Red 26 (C.I. 16150), Food Red 1 (C.I. 14700), Acid Red 88 (C.I. 15620), Acid Orange 20 (C.I. 14600), Acid Yellow 40 (C.I. 18950), Acid Yellow 1 (C.I. 10316), Acid Yellow 36 (C.I. 13065), Acid Yellow 11 (C.I. 18820), Acid Green 1 (C.I. 10020), Acid Green 3 (C.I. 42085), Acid Violet 43 (C.I. 60730), Acid Black 1 (C.I. 20470), Acid Black 52 (C.I. 15711), Acid Blue 1 (C.I. 42045), Acid Blue 3 (C.I. 42051), Acid Blue 62 (C.I. 62045), Acid Brown 13 (C.I. 10410), Acid Green 50 (C.I. 44090), Acid Orange 3 (C.I. 10385), Acid Orange 6 (C.I. 14270), Acid Red 14 (C.I. 14720), Acid Red 35 (C.I. 18065), Acid Red 73 (C.I. 27290), Acid Red 184 (C.I. 15685), and Brilliant Black 1 (C.I. 28440).

Illustrative of the basic dyes are Basic Blue 7 (C.I. 42595), Basic Blue 26 (C.I. 44045), Basic Blue 99 (C.I. 56059), Basic Violet 10 (C.I. 45170), Basic Violet 14 (C.I. 42515), Basic Brown 16 (C.I. 12250), Basic Brown 17 (C.I. 12251), Basic Red 2 (C.I. 50240), Basic Red 22 (C.I. 11055), Basic Red 76 (C.I. 12245), Basic Red 118 (C.I. 12251:1), and Basic Yellow 57 (C.I. 12719); basic dyes each having a quaternized nitrogen atom in a side chain of an aromatic ring as disclosed in JP-B-58002204, JP-A-09118832 or the like; and basic dyes each having a quaternized nitrogen atom and —$Z^1$=$Z^2$— bond ($Z^1$ and $Z^2$ each independently represents a nitrogen atom or a —CH= group), which may be nonlocalized, and respectively represented by the following formulas, as disclosed in Japanese Language Laid-open Publication (PCT) No. HEI 10-502946 (JP-A-10502946), JP-A-10182379, JP-A-11349457, etc.:

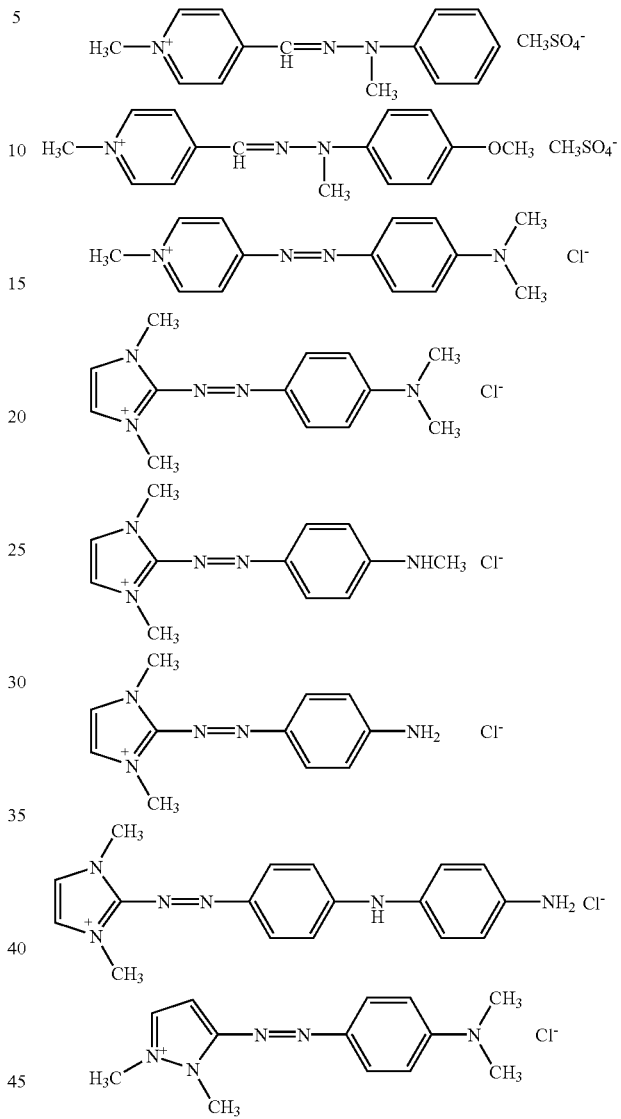

Illustrative of direct dyes other than acidic dyes or basic dyes are 2-amino-3-nitrophenol, 2-amino-4-nitrophenol, 2-amino-5-nitrophenol, 4-amino-3-nitrophenol, 2-amino-6-chloro-4-nitrophenol, 4-hydroxypropylamino-3-nitrophenol, 3-nitro-p-hydroxyethylaminophenol, 2-nitro-p-phenylene-diamine, 4-nitro-o-phenylenediamine, 4-nitro-m-phenylene-diamine, 6-nitro-o-toludine, 6-nitro-p-toluidine, hydroxyethyl-2-nitro-p-toluidine, N,N'-bis(2-hydroxyethyl)-2-nitro-p-phenylenediamine, 2-chloro-5-nitro-N-hydroxyethyl-p-phenylenediamine, 2-nitro-5-glyceryl-methylaniline, 3-methylamino-4-nitrophenoxyethanol, N-ethyl-3-nitroPABA, picramic acid, 2-hydroxyethylpicramic acid, 4-nitrophenylaminoethylurea, Solvent Violet 13 (C.I. 60725), Solvent Yellow 44 (C.I. 56200), Disperse Red 17 (C.I. 11210), Disperse Violet 1 (C.I. 61100), Disperse Violet 4 (C.I. 61105), Disperse Blue 3 (C.I. 61505), Disperse Blue 7 (C.I. 62500), HC Blue No. 2, HC Blue No. 8, HC Orange No. 1, HC Orange No. 2, HC Red No. 1, HC Red No. 3, HC Red No. 7, HC Red No. 8, HC Red No. 10, HC Red No. 11, HC Red No. 13, HC Red No. 16, HC Violet No. 2, HC Yellow No. 2, HC Yellow No. 5, HC Yellow No. 6, HC Yellow No. 7, HC Yellow No. 9, and HC Yellow No. 12.

These direct dyes can be used either singly or in combination. The content of the direct dye may be from 0.001 to 5 wt. % based on the whole composition formed in combination of the first pack and the second pack, with 0.01 to 4 wt. % being particularly preferred.

In the hair bleach or hair dye according to the present invention, a fragrance may be incorporated. As the hair bleach or hair dye according to the present invention can bring about sufficient bleaching or dyeing effect even when ammonium is not used as an alkalizing agent, it has a merit in that a high degree of freedom can be enjoyed upon perfumery, thereby making it easier to impart various fragrances such as fruity fragrances and floral fragrances.

To the hair bleach or hair dye according to the present invention, ingredients commonly employed in the field of cosmetics can be added to extents not impairing the effects of the present invention, in addition to the above-described ingredients. Illustrative of such optional ingredients are natural or synthetic, high molecular compounds, fatty acids, oils and fats, hydrocarbons, higher alcohols, monohydric or polyhydric alcohols, silicone derivatives, nonionic surfactants, amine oxides, amino acid derivatives, protein derivatives, preservatives, metal scavengers, oxidation inhibitors, stabilizers for hydrogen peroxide, plant extracts, vitamins, colorants, pigments, UV absorbers, and pH adjusters.

Like oxidative hair bleaches or hair colors widely employed these days, the hair bleach or hair color according to the present invention can be provided as a two-pack type hair bleach or hair color comprising a first pack with an alkalizing agent contained therein and a second pack with an oxidizing pack contained therein. These first and second packs are mixed preferably at a ratio of from 2:1 to 1:3 (weight ratio) upon use. These first pack and second pack can be prepared by methods known per se in the art. No particular limitation is imposed on their preparation forms. For example, they can be formed into solutions, emulsions, creams, gels, pastes, mousses, or the like. As a still further alternative, they can be prepared into aerosol forms.

The pH of the hair bleach or hair dye according to the present invention at the stage of its use (in other words, after the first pack and the second pack are mixed together) may be from 8 to 12, with 8.5 to 11 being preferred. A pH lower than 8 cannot bring about the effects of the present invention to full extents, while a pH higher than 12 leads to strong irritation to the scalp. pHs outside this range are, therefore, improper from the practical viewpoint.

To bleach or dye hair with the hair bleach or hair dye according to the present invention, it is only necessary, for example, to apply the hair bleach or hair dye according to the present invention to the hair at a temperature of from 15 to 45° C. and after an acting time of from 1 to 50 minutes, preferably from 3 to 30 minutes, to wash the hair and then to dry the same.

EXAMPLES

Example 1

Oxidative hair bleaches shown in Tables 1 and 2 were formulated, and their bleaching performances were ranked.

(Formulation Method)

The hair bleach as Invention Product 1 was formulated as will be described hereinafter (the first pack and the second pack were used by mixing them in the same weights, respectively). In addition, the hair bleaches as Invention Products 2–4 and Comparative Products 1–9 were also formulated following the formulation method of Invention Product 1.

First Pack

To 2-benzyloxyethanol (24 g), polyoxyethylene (3) tridecyl ether (20 g), a 68 wt. % aqueous solution (15 g) of sodium polyoxyethylene (2) lauryl ether sulfate and a 30 wt. % aqueous solution (26.7 g) of lauramidopropylbetaine were added, followed by stirring into a homogeneous mixture. Water (10.3 g) and monoethanolamine (4 g) were added further, and the resulting mixture was stirred to give a homogeneous mixture.

Second Pack

To water (31.9 g), a 68 wt. % aqueous solution (35 g) of sodium polyoxyethylene (2) lauryl ether sulfate, polyoxyethylene (3) tridecyl ether (16 g) and a 35 wt. % aqueous solution (17.1 g) of hydrogen peroxide were added, followed by stirring into a homogeneous mixture.

(Ranking Method)

Using hair collected from a Japanese and having no history of chemical treatment, eight tresses, each of 10 g, were provided. Then, they were each evenly coated with corresponding one sample (7 g) selected from of Invention Products 1–2 and Comparative Products 1–5. After the tresses were allowed to stand for 15 minutes in a constant temperature chamber controlled at 30° C., they were rinsed with tepid water of 30° C., shampooed and rinsed, and then dried. The thus-treated tresses were compared with the remaining one tress, and the degrees of their bleaching were ranked by a panel of 10 experts on the basis of the below-described standard. The results are presented in terms of total scores in Tables 1 and 2.

(Ranking Standard)

4: Bleached into a significantly light color.
3: Bleached into a light color.
2: Bleached into a slightly light color.
1: Color shade did not change substantially.
0: Color shade did not change at all.

TABLE 1

| | Invention product | | Comparative product | | | | |
|---|---|---|---|---|---|---|---|
| | 1 | 2 | 1 | 2 | 3 | 4 | 5 |
| Composition of the first pack + the second pack (parts by weight) | | | | | | | |
| Sodium polyoxyethylene (2) lauryl ether sulfate | 17 | 17 | 17 | 17 | 17 | 17 | 17 |
| Lauramidopropylbetaine | 4 | 4 | 4 | 4 | 4 | 4 | 4 |
| Polyoxyethylene (3) tridecyl ether | 18 | 18 | 18 | 18 | 18 | 18 | 18 |
| Monoethanolamine | 2 | 2 | 2 | 2 | 2 | 2 | 5 |
| Ammonia | — | 0.56 | — | — | — | 0.56 | 0.56 |
| Hydrogen peroxide | 3 | 3 | 3 | 3 | 3 | 3 | 3 |
| Benzyloxyethanol (log P = 1.2) | 12 | 12 | 4 | — | — | — | — |
| Ethanol (log P = −0.3) | — | — | — | 12 | — | 12 | 12 |

TABLE 1-continued

|  | Invention product | | Comparative product | | | | |
|---|---|---|---|---|---|---|---|
|  | 1 | 2 | 1 | 2 | 3 | 4 | 5 |
| Propylene glycol (log P = −1.1) | — | — | — | — | 12 | — | — |
| Water | 44 | 43.44 | 52 | 44 | 44 | 43.44 | 40.44 |
| Ranking of bleaching power (40 points max.) | 31 | 38 | 20 | 11 | 10 | 13 | 19 |

TABLE 2

|  | Invention product | | Comparative product | | | |
|---|---|---|---|---|---|---|
|  | 3 | 4 | 6 | 7 | 8 | 9 |
| Composition of the first pack + the second pack (parts by weight) | | | | | | |
| Sodium polyoxyethylene (2) lauryl ether sulfate | 15 | 15 | 3 | 3 | 15 | 15 |
| Lauramidopropylbetaine | 4 | 4 | 4 | 4 | 4 | 4 |
| Polyoxyethylene (3) tridecyl ether | 15 | 15 | 15 | 15 | 2 | 2 |
| Benzyl alcohol (log P = 1.1) | 12 | 12 | 12 | 12 | 2 | 2 |
| Monoethanolamine | 2 | 2 | 2 | 2 | 2 | 2 |
| Ammonia | — | 0.56 | — | 0.56 | — | 0.56 |
| Hydrogen peroxide | 3 | 3 | 3 | 3 | 3 | 3 |
| Water | 44 | 48.44 | 61 | 60.44 | 72 | 71.44 |
| Ranking of bleaching power (40 points max.) | 30 | 37 | 17 | 20 | 11 | 14 |

As is evident from Tables 1 and 2, the invention products had excellent bleaching performance. In particular, Invention Products 1 and 3 did not give unpleasant feeling upon bleaching as they were free of ammonia.

Example 2 Bleach composition (the first pack and the second pack were used by mixing them in the same weights)

(wt. %)

First pack

| Sodium polyoxyethylene (2) lauryl ether sulfate | 15 |
| Coconut fatty acid diethanolamide | 40 |
| Benzyl alcohol | 25 |
| 28 wt. % Aqueous ammonia | 7 |
| Water | 13 |

Second pack

| Sodium polyoxyethylene (2) lauryl ether sulfate | 20 |
| Coconut fatty acid diethanolamide | 2 |
| 35 wt. % Hydrogen peroxide solution | 17 |
| 75 wt. % Phosphoric acid solution | 0.3 |
| Water | 60.7 |

Example 3 Bleach composition (the first pack and the second pack were used by mixing them in the same weights)

(wt. %)

First pack

| Polyoxyethylene (9) nonyl phenyl ether | 15 |
| Sodium lauroyl glutamate | 5 |
| Oleic acid | 5 |
| Polyoxyethylene (9) tridecyl ether | 30 |
| Benzyl alcohol | 25 |
| 28 wt. % Aqueous ammonia | 7 |
| Water | 13 |

Second pack

| Sodium polyoxyethylene (2) lauryl ether sulfate | 20 |
| Polyoxyethylene (2) tridecyl ether | 2 |
| 35 wt. % Hydrogen peroxide solution | 17 |
| 75 wt. % Phosphoric acid solution | 0.3 |
| Water | 60.7 |

Example 4 Hair dye composition (the first pack and the second pack were used by mixing them in the same weights)

(wt. %)

First pack

| Sodium polyoxyethylene (2) lauryl ether sulfate | 20 |
| Oleic acid | 5 |
| 2-Benzyloxyethanol | 20 |
| Monoethanolamine | 5 |
| Anhydrous sodium sulfite | 0.4 |
| 1-(2-Hydroxyethyl)-2,5-diaminobenzene dihydrochloride | 1.34 |
| 2,4-Diaminophenoxyethanol | 1 |
| Water | 47.26 |

Second pack

| Sodium polyoxyethylene (2) lauryl ether sulfate | 20 |
| Oleyl alcohol | 20 |
| Polyoxyethylene (25) octyl dodecyl ether | 25 |
| 2-Benzyloxyethanol | 15 |
| 35 wt. % Hydrogen peroxide solution | 17 |
| 75 wt. % Phosphoric acid solution | 0.3 |
| Water | 2.7 |

Example 5 Hair dye composition (the first pack and the second pack were used by mixing them in the same weights)

(wt. %)

First pack

| Sodium polyoxyethylene (2) lauryl ether sulfate | 12 |
| Polyoxyethylene (3) tridecyl ether | 39 |
| Ethylene glycol mono-n-butyl ether | 20 |
| Monoethanolamine | 5 |
| Anhydrous sodium sulfite | 0.4 |
| o-Aminophenol | 1.5 |
| Water | 22.1 |

Second pack

| Sodium polyoxyethylene (2) lauryl ether sulfate | 22 |
| Polyoxyethylene (3) tridecyl ether | 2 |
| 35 wt. % Hydrogen peroxide solution | 17 |
| 75 wt. % Phosphoric acid solution | 0.3 |
| Water | 58.7 |

Example 6 Hair dye composition (the first pack and the second pack were used by mixing them in the same weights)

(wt. %)

First pack

| Sodium lauroyl glutamate | 5 |
| Sodium lauroyl sulfate | 5 |
| Sodium alkane sulfonate | 3 |
| Polyoxyethylene (3) tridecyl ether | 39 |
| 2-Benzyloxyethanol | 25 |
| Monoethanolamine | 4 |
| 28 wt. % Aqueous ammonia | 3.5 |
| Anhydrous sodium sulfite | 0.4 |
| Toluene-2, 5-diamine | 1 |
| m-Aminophenol | 1 |

-continued

| | |
|---|---|
| "Merquat 550" (product of BF Goodrich Co.) | 4.5 |
| Water | 8.6 |
| Second pack | |
| Sodium polyoxyethylene (2) lauryl ether sulfate | 15 |
| Polyoxyethylene (9) lauryl ether | 5 |
| 35 wt. % Hydrogen peroxide solution | 17 |
| 75 wt. % Phosphoric acid solution | 0.3 |
| Water | 62.7 |

Example 7 Hair dye composition (the first pack and the second pack were used by mixing them in the same weights)

| | (wt. %) |
|---|---|
| First pack | |
| Sodium polyoxyethylene (2) lauryl ether sulfate | 12 |
| Polyoxyethylene (3) tridecyl ether | 39 |
| Benzyl alcohol | 20 |
| Monoethanolamine | 5 |
| "Merquat 280" (product of BF Goodrich Co.) | 1.3 |
| "Merquat 295" (product of BF Goodrich Co.) | 0.6 |
| Anhydrous sodium sulfite | 0.4 |
| N,N-Bis(2-hydroxyethyl)-p-phenylenediamine sulfate | 2.15 |
| Resorcin | 0.8 |
| Water | 18.75 |
| Second pack | |
| Sodium polyoxyethylene (2) lauryl ether sulfate | 22 |
| Polyoxyethylene (3) tridecyl ether | 2 |
| 35 wt. % Hydrogen peroxide solution | 17 |
| 75 wt. % Phosphoric acid solution | 0.3 |
| Water | 58.7 |

Example 8 Hair dye composition (the first pack and the second pack were used by mixing them in the same weights)

| | (wt. %) |
|---|---|
| First pack | |
| Sodium polyoxyethylene (2) lauryl ether sulfate | 12 |
| Polyoxyethylene (3) tridecyl ether | 39 |
| 2-Benzyloxyethanol | 24 |
| Monoethanolamine | 4 |
| 28 wt. % Aqueous ammonia | 1 |
| Acid Red 52 | 0.6 |
| Water | 19.4 |
| Second pack | |
| Sodium polyoxyethylene (2) lauryl ether sulfate | 22 |
| Polyoxyethylene (3) tridecyl ether | 2 |
| 35 wt. % Hydrogen peroxide solution | 17 |
| 75 wt. % Phosphoric acid solution | 0.3 |
| Water | 58.7 |

Example 9 Hair dye composition (the first pack and the second pack were used by mixing them in the same weights)

| | (wt. %) |
|---|---|
| First pack | |
| Sodium polyoxyethylene (2) lauryl ether sulfate | 2 |
| Polyoxyethylene (9) nonyl phenyl ether | 15 |
| Polyoxyethylene (9) tridecyl ether | 30 |
| Benzyl alcohol | 25 |
| Monoethanolamine | 3.5 |
| 28 wt. % Aqueous ammonia | 1 |
| Basic Red 76 | 0.5 |
| Water | 23 |

-continued

| | |
|---|---|
| Second pack | |
| Polyoxyethylene (9) tridecyl ether | 22 |
| 35 wt. % Hydrogen peroxide solution | 17 |
| 75 wt. % Phosphoric acid solution | 0.3 |
| Water | 60.7 |

Example 10 Hair dye composition (the first pack and the second pack were used by mixing them in the same weights)

| | (wt. %) |
|---|---|
| First pack | |
| Sodium polyoxyethylene (2) lauryl ether sulfate | 7 |
| Sodium α-olefinsulfonate | 6 |
| Coconut fatty acid diethanolamide | 20 |
| Polyoxyethylene (3) tridecyl ether | 21 |
| 2-Benzyloxyethanol | 22 |
| 28 wt. % Aqueous ammonia | 1 |
| Isopropanolamine | 4 |
| Anhydrous sodium sulfite | 0.4 |
| "Catinal LC-100" (product of Union Carbide Corp.) | 0.3 |
| o-Aminophenol | 1.5 |
| Disperse Blue 7 | 0.2 |
| Water | 16.6 |
| Second pack | |
| Sodium polyoxyethylene (2) lauryl ether sulfate | 20 |
| Polyoxyethylene (20) lauryl ether | 2 |
| 35 wt. % Hydrogen peroxide solution | 17 |
| 75 wt. % Phosphoric acid solution | 0.3 |
| Water | 60.7 |

Example 11 Hair dye composition (the first pack and the second pack were used by mixing them in the same weights)

| | (wt. %) |
|---|---|
| First pack | |
| Sodium alkane sulfonate | 7 |
| Lauramidopropylbetaine | 5 |
| Polyoxyethylene (9) lauryl ether | 25 |
| "Polyether-modified Silicone KF-6005" (product of Shin-Etsu Chemical Co., Ltd.) | 0.5 |
| Ethylene glycol mono-n-butyl ether | 20 |
| "Catinal LC-100" (product of Union Carbide Corp.) | 0.4 |
| 28 wt. % Aqueous ammonia | 1 |
| Isopropanolamine | 4 |
| Anhydrous sodium sulfite | 0.4 |
| p-Nitro-o-phenylenediamine | 0.3 |
| p-Aminophenol | 0.9 |
| p-Amino-o-cresol | 1 |
| Water | 34.5 |
| Second pack | |
| Sodium polyoxyethylene (2) lauryl ether sulfate | 12 |
| Sodium lauroyl glutamate | 5 |
| Diethylene glycol mono-n-butyl ether | 5 |
| "Polyether-modified Silicone KF-6005" (product of Shin-Etsu Chemical Co., Ltd.) | 0.5 |

-continued

| | (wt. %) |
|---|---|
| 35 wt. % Hydrogen peroxide solution | 17 |
| 75 wt. % Phosphoric acid solution | 0.3 |
| Water | 60.2 |

Example 12 Hair dye composition (the first pack and the second pack were used by mixing them in the same weights)

| | (wt. %) |
|---|---|
| First pack | |
| Sodium polyoxyethylene (2) lauryl ether sulfate | 2 |
| Polyoxyethylene (9) nonyl phenyl ether | 15 |
| Polyoxyethylene (9) tridecyl ether | 30 |
| Benzyl alcohol | 25 |
| Monoethanolamine | 5 |
| Anhydrous sodium sulfite | 0.4 |
| p-Aminophenol | 0.9 |
| p-Amino-o-cresol | 1 |
| Basic Red 22 | 0.2 |
| Water | 20.5 |
| Second pack | |
| Polyoxyethylene (9) tridecyl ether | 22 |
| 35 wt. % Hydrogen peroxide solution | 17 |
| 75 wt. % Phosphoric acid solution | 0.3 |
| Water | 60.7 |

Example 13 Bleach composition (the first pack and the second pack were used by mixing them in the same weights)

| | (wt. %) |
|---|---|
| First pack | |
| Polyoxyethylene (9) nonyl phenyl ether | 15 |
| Sodium lauroyl glutamate | 5 |
| Oleyl alcohol | 3 |
| Polyoxyethylene (9) tridecyl ether | 30 |
| 2-Benzyloxyethanol | 18 |
| 28 wt. % Aqueous ammonia | 7 |
| Water | 22 |
| Second pack | |
| Sodium polyoxyethylene (2) lauryl ether sulfate | 20 |
| Polyoxyethylene (2) tridecyl ether | 2 |
| 35 wt. % Hydrogen peroxide solution | 17 |
| 75 wt. % Phosphoric acid solution | 0.3 |
| Water | 60.7 |

Example 14 Bleach composition (the first pack and the second pack were used by mixing them in the same weights)

| | (wt. %) |
|---|---|
| First pack | |
| Sodium polyoxyethylene (2) lauryl ether sulfate | 15 |
| Coconut fatty acid diethanolamide | 40 |
| 2-Benzyloxyethanol | 14 |
| 28 wt. % Aqueous ammonia | 7 |
| Water | 24 |
| Second pack | |
| Sodium polyoxyethylene (2) lauryl ether sulfate | 20 |
| Coconut fatty acid diethanolamide | 2 |
| 35 wt. % Hydrogen peroxide solution | 17 |

-continued

| | (wt. %) |
|---|---|
| 75 wt. % Phosphoric acid solution | 0.3 |
| Water | 60.7 |

Example 15 Hair dye composition (the first pack and the second pack were used by mixing them in the same weights)

| | (wt. %) |
|---|---|
| First pack | |
| Sodium polyoxyethylene (2) lauryl ether sulfate | 20 |
| Oleyl alcohol | 3 |
| 2-Benzyloxyethanol | 20 |
| Monoethanolamine | 5 |
| Anhydrous sodium sulfite | 0.4 |
| p-Aminophenol | 0.9 |
| p-Amino-o-cresol | 1 |
| Water | 49.7 |
| Second pack | |
| Sodium polyoxyethylene (2) lauryl ether sulfate | 20 |
| Oleyl alcohol | 20 |
| Polyoxyethylene (25) octyl dodecyl ether | 25 |
| 2-Benzyloxyethanol | 15 |
| 35 wt. % Hydrogen peroxide solution | 17 |
| 75 wt. % Phosphoric acid solution | 0.3 |
| Water | 2.7 |

Example 16 Hair dye composition (the first pack and the second pack were used by mixing them in the same weights)

| | (wt. %) |
|---|---|
| First pack | |
| Sodium polyoxyethylene (2) lauryl ether sulfate | 12 |
| Polyoxyethylene (3) tridecyl ether | 39 |
| Ethylene glycol mono-n-butyl ether | 20 |
| Monoethanolamine | 5 |
| Anhydrous sodium sulfite | 0.4 |
| o-Aminophenol | 1.5 |
| Water | 22.1 |
| Second pack | |
| Sodium polyoxyethylene (2) lauryl ether sulfate | 22 |
| Polyoxyethylene (3) tridecyl ether | 2 |
| 35 wt. % Hydrogen peroxide solution | 17 |
| 75 wt. % Phosphoric acid solution | 0.3 |
| Water | 58.7 |

Example 17 Hair dye composition (the first pack and the second pack were used by mixing them in the same weights)

| | (wt. %) |
|---|---|
| First pack | |
| Sodium polyoxyethylene (2) lauryl ether sulfate | 12 |
| Polyoxyethylene (3) tridecyl ether | 39 |
| Benzyl alcohol | 20 |
| Monoethanolamine | 5 |
| "Merquat 280" (product of BF Goodrich Co.) | 1.3 |
| "Merquat 295" (product of BF Goodrich Co.) | 0.6 |
| Anhydrous sodium sulfite | 0.4 |
| N,N-Bis(2-hydroxyethyl)-p-phenylenediamine sulfate | 3.24 |
| m-Aminophenol | 1.2 |
| Water | 17.26 |
| Second pack | |
| Sodium polyoxyethylene (2) lauryl ether sulfate | 22 |
| Polyoxyethylene (3) tridecyl ether | 2 |
| 35 wt. % Hydrogen peroxide solution | 17 |

| -continued | |
|---|---|
| 75 wt. % Phosphoric acid solution | 0.3 |
| Water | 58.7 |

Example 18 Hair dye composition (the first pack and the second pack were used by mixing them in the same weights)

| | (wt. %) |
|---|---|
| First pack | |
| Sodium lauroyl glutamate | 5 |
| Sodium lauroyl sulfate | 5 |
| Sodium alkane sulfonate | 3 |
| Polyoxyethylene (3) tridecyl ether | 39 |
| 2-Benzyloxyethanol | 25 |
| Monoethanolamine | 4 |
| 28 wt. % Aqueous ammonia | 3.5 |
| Anhydrous sodium sulfite | 0.4 |
| Toluene-2,5-diamine | 1.8 |
| 2-Methylresorcin | 1.8 |
| "Merquat 550" (product of BF Goodrich Co.) | 4.5 |
| Water | 7 |
| Second pack | |
| Sodium polyoxyethylene (2) lauryl ether sulfate | 15 |
| Polyoxyethylene (9) lauryl ether | 5 |
| 35 wt. % Hydrogen peroxide solution | 17 |
| 75 wt. % Phosphoric acid solution | 0.3 |
| Water | 62.7 |

Example 19 Hair dye composition (the first pack and the second pack were used by mixing them in the same weights)

| | (wt. %) |
|---|---|
| First pack | |
| Sodium alkane sulfonate | 7 |
| Lauramidopropylbetaine | 5 |
| Polyoxyethylene (9) lauryl ether | 25 |
| "Polyether-modified Silicone KF-6005" (product of Shin-Etsu Chemical Co., Ltd.) | 0.5 |
| Ethylene glycol mono-n-butyl ether | 20 |
| "Catinal LC-100" (product of Union Carbide Corp.) | 0.4 |
| 28 wt. % Aqueous ammonia | 1 |
| Isopropanolamine | 4 |
| Anhydrous sodium sulfite | 0.4 |
| Acid Yellow 3 | 0.3 |
| p-Aminophenol | 0.9 |
| p-Amino-o-cresol | 1 |
| Water | 34.5 |
| Second pack | |
| Sodium polyoxyethylene (2) lauryl ether sulfate | 12 |
| Sodium lauroyl glutamate | 5 |
| Diethylene glycol mono-n-butyl ether | 5 |
| "Polyether-modified Silicone KF-6005" (product of Shin-Etsu Chemical Co., Ltd.) | 0.5 |
| 35 wt. % Hydrogen peroxide solution | 17 |
| 75 wt. % Phosphoric acid solution | 0.3 |
| Water | 60.2 |

Example 20 Hair dye composition (the first pack and the second pack were used by mixing them in the same weights)

| | (wt. %) |
|---|---|
| First pack | |
| Sodium polyoxyethylene (2) lauryl ether sulfate | 7 |
| Sodium α-olefinsulfonate | 6 |
| Coconut fatty acid diethanolamide | 20 |
| Polyoxyethylene (3) tridecyl ether | 21 |
| 2-Benzyloxyethanol | 10 |
| 28 wt. % Aqueous ammonia | 1 |

| -continued | |
|---|---|
| Isopropanolamine | 4 |
| Anhydrous sodium sulfite | 0.4 |
| "Catinal LC-100" (product of Union Carbide Corp.) | 0.3 |
| o-Aminophenol | 1.5 |
| Disperse Blue 3 | 0.2 |
| Water | 28.6 |
| Second pack | |
| Sodium polyoxyethylene (2) lauryl ether sulfate | 20 |
| Polyoxyethylene (20) lauryl ether | 2 |
| 35 wt. % Hydrogen peroxide solution | 17 |
| 75 wt. % Phosphoric acid solution | 0.3 |
| Water | 60.7 |

Example 21 Hair dye composition (the first pack and the second pack were used by mixing them in the same weights)

| | (wt. %) |
|---|---|
| First pack | |
| Sodium polyoxyethylene (2) lauryl ether sulfate | 12 |
| Polyoxyethylene (3) tridecyl ether | 39 |
| Benzyloxyethanol | 24 |
| Monoethanolamine | 4 |
| 28 wt. % Aqueous ammonia | 1 |
| Acid Orange 7 | 0.5 |
| Water | 19.5 |
| Second pack | |
| Sodium polyoxyethylene (2) lauryl ether sulfate | 22 |
| Polyoxyethylene (3) tridecyl ether | 2 |
| 35 wt. % Hydrogen peroxide solution | 17 |
| 75 wt. % Phosphoric acid solution | 0.3 |
| Water | 58.7 |

The bleaches and hair dyes of Examples 2–21 had excellent bleaching or dyeing power and further, were free of an irritating odor or irritation to the scalp upon application.

The invention claimed is:

1. An oxidative hair bleach comprising a first pack with an alkalizing agent contained therein and a second pack with an oxidizing agent contained therein, wherein said oxidative hair bleach comprises the following ingredients (A), (B), (C), (D), and (E) in the following proportions in a whole composition after mixing said first pack and said second pack together, and has a pH of from 8 to 12:
   (A) benzyl alcohol or benzyloxyethanol: 8 to 40 wt. %
   (B) said alkalizing agent: 0.1 to 10 wt. %
   (C) said oxidizing agent: 0.1 to 12 wt. % as calculated in terms of hydrogen peroxide
   (D) water: 20 to 60 wt. % and
   (E) an anionic surfactant or ampholytic surfactant in a proportion of from 5 to 60 wt. % in said whole composition after mixing said first pack and said second pack together.

2. A bleach according to claim 1, further comprising, as an ingredient (F), a quaternized-nitrogen-atom-containing polymer in a proportion of 2.5 wt. % or less in said whole composition after mixing said first pack and said second pack together.

3. A method for bleaching hair, which comprises applying to said hair a bleach according to claim 1.

4. A method for bleaching hair, which comprises applying to said hair the bleach according to claim 2.

5. A bleach according to claim 1, further comprising as an ingredient (F), a quaternized-nitrogen-atom-containing polymer in a proportion of from 0.3 to 2.5 wt % in said whole composition after mixing said first pack and said second pack together.

6. A bleach according to claim 1, wherein (A) ranges from 10 to 40 wt. %.

7. A bleach according to claim 1, wherein (A) ranges from 10 to 25 wt. %.

8. A bleach according to claim 1, wherein (B) ranges from 0.5 to 5 wt. %.

9. A bleach according to claim 1, wherein (B) ranges from 1 to 3 wt. %.

10. A bleach according to claim 1, wherein (C) ranges from 2 to 12 wt. %.

11. A bleach according to claim 1, wherein (D) ranges from 30 to 55 wt. %.

12. A bleach according to claim 1, wherein (E) ranges from 10 to 30 wt. %.

13. A bleach according to claim 2, wherein (F) ranges from 0.3 to 2 wt. %.

14. A bleach according to claim 2, wherein (F) ranges from 0.3 to 1 wt. %.

15. A bleach according to claim 1, wherein the pH ranges from 8.5 to 11.

16. A method for bleaching hair, which comprises applying to said hair the bleach according to claim 6.

17. A method for bleaching hair, which comprises applying to said hair the bleach according to claim 7.

18. A method for bleaching hair, which comprises applying to said hair the bleach according to claim 11.

* * * * *